United States Patent [19]
Ghawi

[11] Patent Number: 5,388,619
[45] Date of Patent: Feb. 14, 1995

[54] CLAMP TIGHTENING DEVICE

[76] Inventor: Roger Ghawi, 26, av. de Charolles, Paray le Monial 71600, France

[21] Appl. No.: 112,242

[22] Filed: Aug. 24, 1993

[30] Foreign Application Priority Data

Aug. 27, 1992 [FR] France ................................ 92 10460

[51] Int. Cl.⁶ .............................................. B21P 9/02
[52] U.S. Cl. .................................. 140/123.6; 140/93.2
[58] Field of Search ........................ 140/57, 93.2, 93.4, 140/123.5, 123.6

[56] References Cited

FOREIGN PATENT DOCUMENTS 1031684  6/1966  United Kingdom .
1587370  4/1981  United Kingdom ............. 140/123.6

Primary Examiner—Lowell A. Larson
Attorney, Agent, or Firm—Dowell & Dowell

[57] ABSTRACT

A device for tightening a collar clamp around an elongated member. The device includes a pair of pivoted arms having distal portions on one side of a pivot axis and, on the other side, handles resiliently urged away from each other. A pawl, pivoted perpendicularly to the arms' pivot axis and disposed in the distal portion of one arm, engages and pulls the collar tongue through an opening in the second arm when the handles are squeezed together. A third arm mounted remotely from the distal portions of the arms actuates a blade to sever the collar tongue once the collar has been tightened sufficiently.

14 Claims, 5 Drawing Sheets

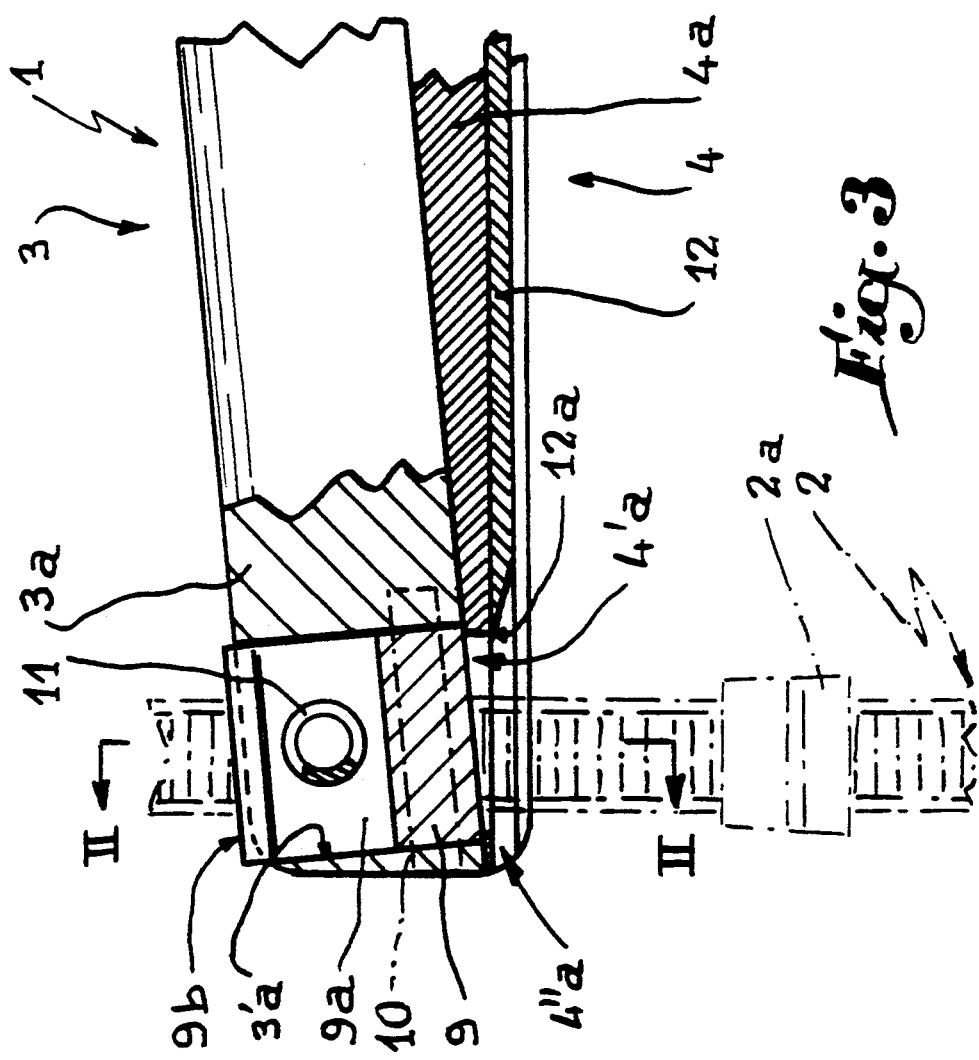
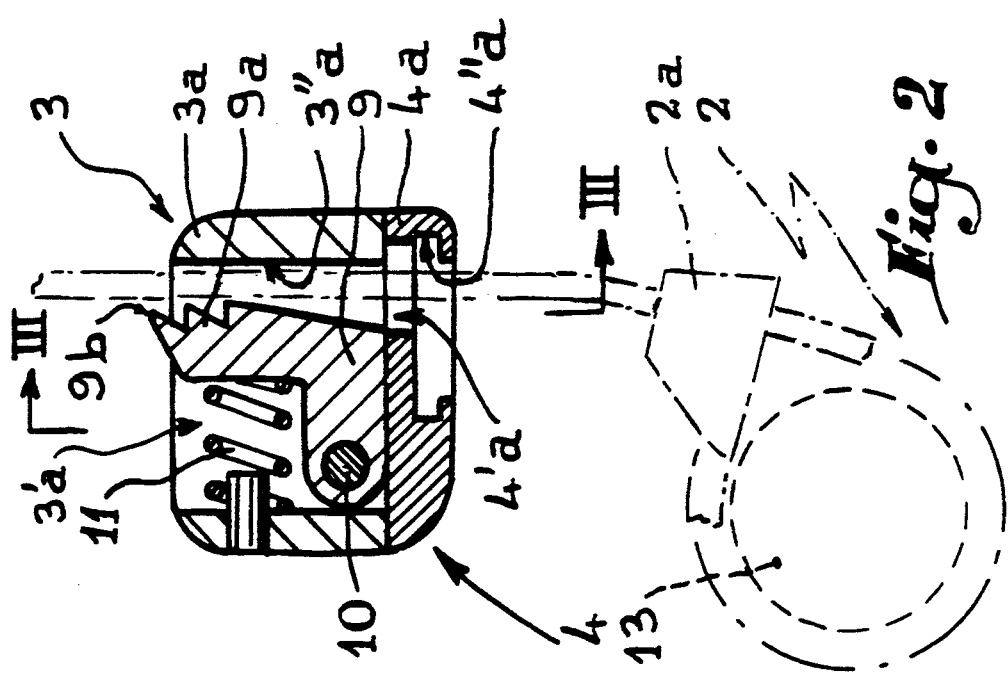

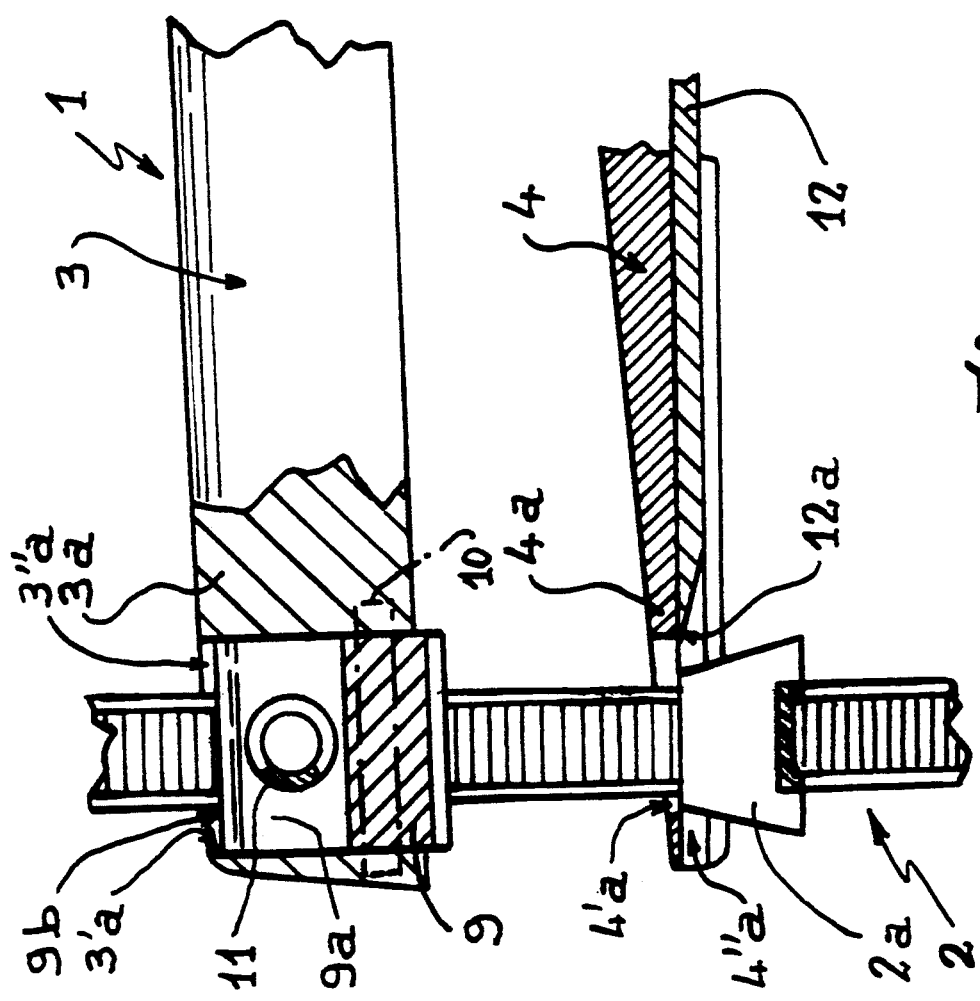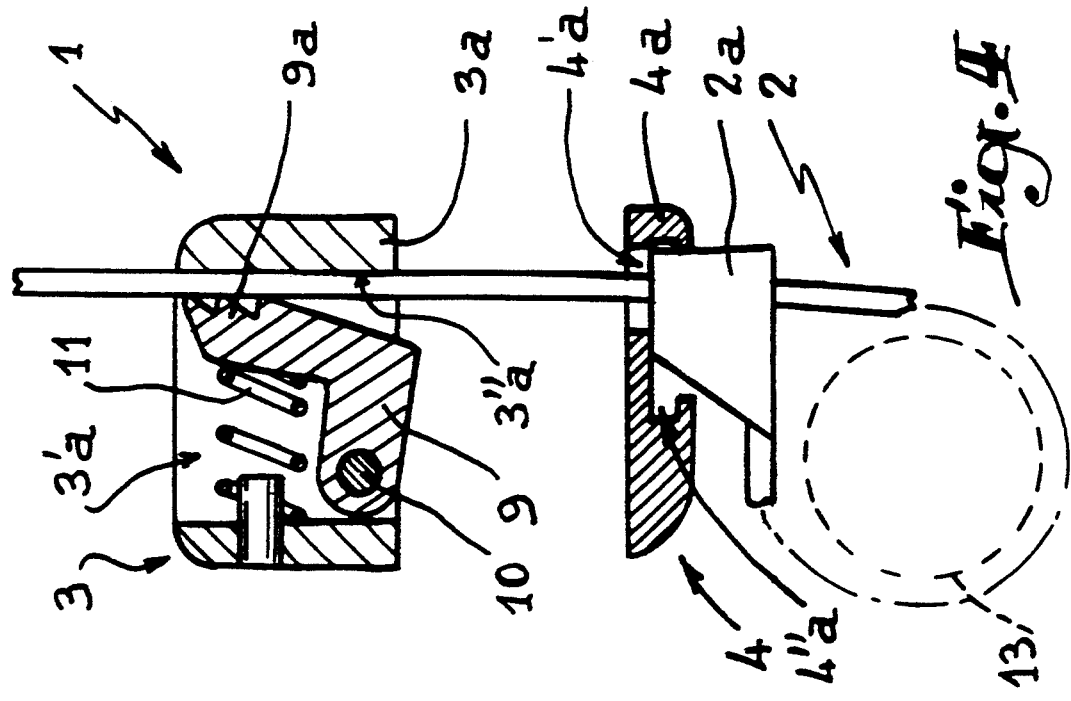

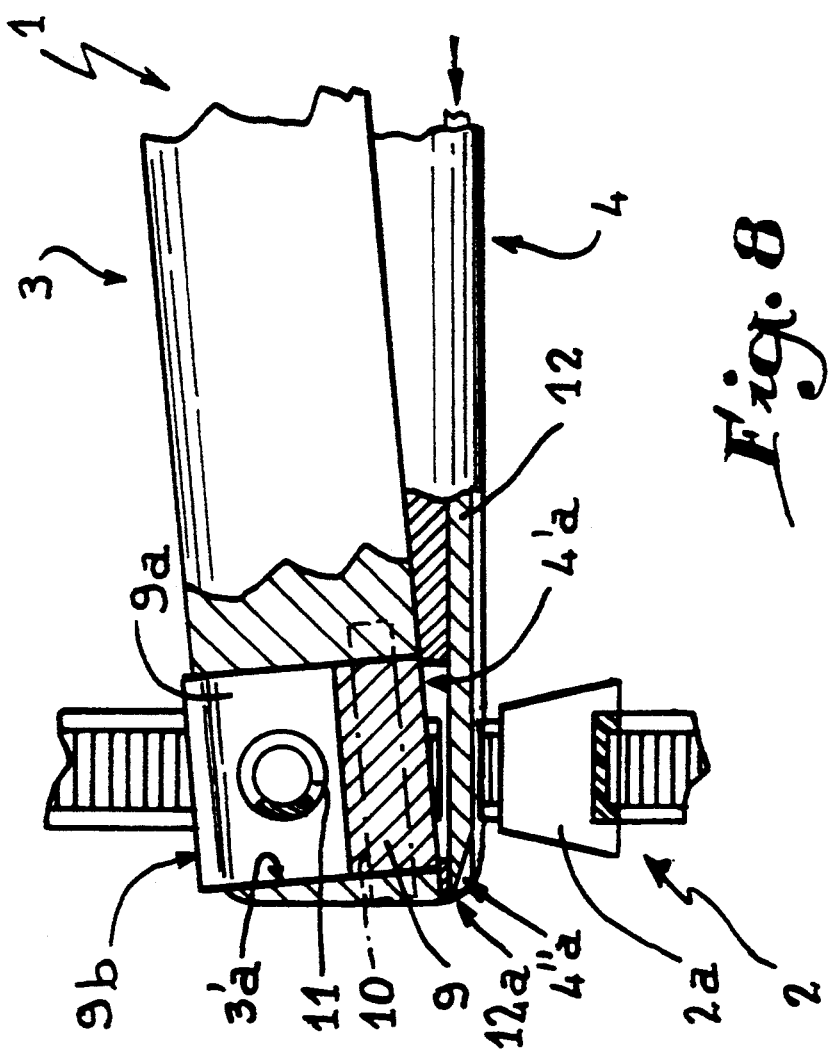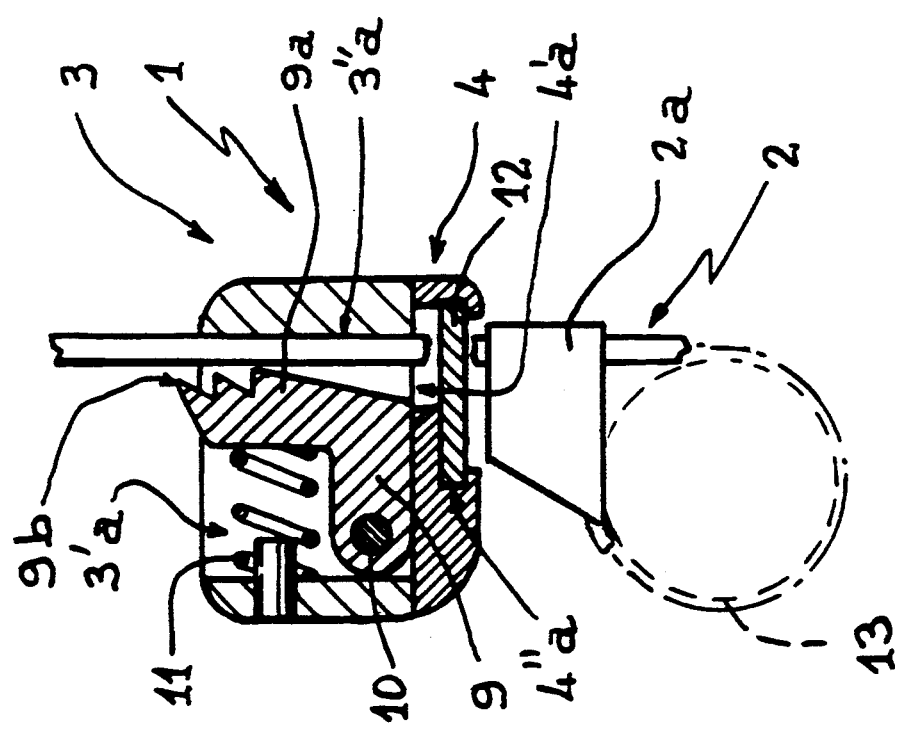

CLAMP TIGHTENING DEVICE

BACKGROUND OF THE INVENTION

1. Field of the Invention

The present invention relates to a device for tightening a clamping collar on an elongated member.

2. History of the Related Art

Clamping collars with slanting teeth are known, with a step made in a passage of a widened end of the collar provided to be traversed by the collar when placed in a loop. Tightening is effected by displacing, little by little, the tongue of the collar in the passage by means of a pawl with a gripping surface that lies in the plane of the collar.

In certain cases, i.e. when the collar must be tightened around an elongated member located in a cavity surrounding this member whose geometrical axis is parallel thereto, the conventional clamp tightening device cannot be used.

It is known, that, in gynecology-obstetrics, it is often necessary to effect a "cerclage." of the cervix of the uterus of a pregnant woman in order to avoid a miscarriage.

Up to the present time, such cerclage is effected by means of yarns surrounding the cervix of the uterus which are engaged in the flesh of the cervix in order to be suitably maintained in place.

It will be readily understood that such an intervention is traumatizing for the patient, all the more so as it requires at least local anaesthetic, with all the inconvenience that this involves.

SUMMARY OF THE INVENTION

The improvements forming the subject matter of the present invention aim at allowing production of a device for tightening a collar disposed on an elongated member when the device is substantially parallel to the longitudinal axis of the elongated member.

A particularly interesting application of the invention is encountered in the cerclage of the cervix of the uterus of a human being or of an animal.

The clamp tightening device according to the invention is provided with two articulated arms, resiliently urged toward each other so that, in a rest position, the opposite inner faces of their distal portions are in abutment against each other, and their handles are spaced apart from each other. The distal portion of the first arm is provided with an opening in which is place a spring biased pivoting pawl having a gripping surface which is, in the rest position of the device, raised in the opening by the distal portion of the second arm, which comprises a second opening located opposite the opening in the first arm.

BRIEF DESCRIPTION OF THE DRAWINGS

The accompanying drawings, given by way of example, will enable the invention, the characteristics that it presents and the advantages that it is capable of procuring, to be more readily understood.

FIG. 2 is a transverse section illustrating the distal portions of the arms of the device in rest position. The collar which the device of FIG. 1 is intended to tighten is shown in broken lines.

FIG. 3 is a section along III—III (FIG. 2). II—II represent the plane of section of FIG. 2, and the collar has been shown in broken lines.

FIG. 4 is a view similar to that of FIG. 2, but illustrating the distal portion of the arms spaced apart in the course of tightening of the collar.

FIG. 5 is a view similar to that of FIG. 3, but corresponding to FIG. 4.

FIG. 7 is a view similar to that of FIG. 2, but showing the severing of the collar by the cutting blade.

FIG. 8 is a view similar to that of FIG. 3, but corresponding to FIG. 7, with the cutting blade in advanced position.

DESCRIPTION OF THE PREFERRED EMBODIMENT

Figure 1:
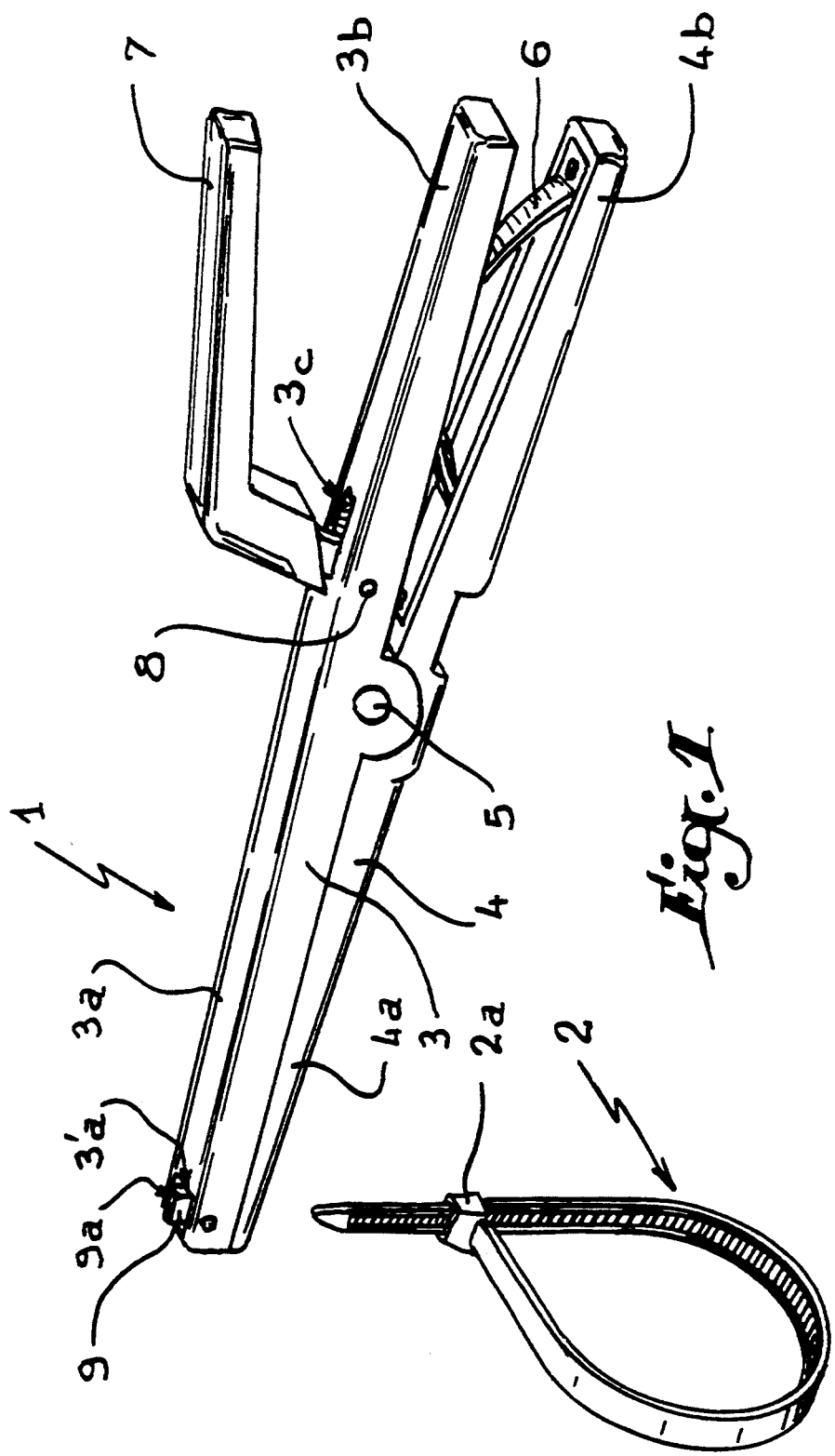
FIG. 1 is a perspective view of a clamp tightening device according to the invention and of a collar that the device is intended to tighten.

FIG. 1 illustrates a device 1 according to the invention which is intended to tighten a collar 2.

The device is provide with two arms 3, 4, articulated about a common pin 5. Each arm comprises a distal portion 3a, 4a, and a handle 3b, 4b, respectively. A leaf spring 6 or the like tends to move the two handles 3b, 4b, apart so that, at rest, the two distal portions 3a, 4a, rest against each other on at least partially plane faces. A lever 7 is articulated on arm 3 about a pin 8 and controls a cutting blade, as will be explained in greater detail hereinafter.

The free end of the jaw 3a is provided with a an opening 3'a (FIG. 2) in which is placed a clamping pawl 9 taking the general form of an L. The end of one of the sides of this pawl is articulated about a longitudinal pin 10 traversing the opening 3'a. The free end of the other side of the pawl is provided with a gripping surface 9a having at least one sharp edge 9b. A compression spring 11 loads the pawl 9 so that its gripping surface 9a tends to come into abutment against a surface 3''a in the opening 3'a. The second arm 4a comprises, opposite the opening 3'a, a second opening 4' which opens out in a longitudinal slide-way 4''a in T-form in which slides a blade 12 (FIG. 3). The cutting edge 12a of this blade is located adjacent the second opening 4'a, in the rest position of the device. As illustrated in FIG. 2, when the two distal portions of the device are closed, the gripping surface 9a of the pawl 9 is maintained at a distance from face 3''a of opening 3'a slightly greater than the thickness of the tongue of the collar 2. The tongue may thus be easily engaged in the distal portions of the clamp after the tongue has traversed the widened end 2a of the collar.

Therefore, after the collar has surrounded an elongated member 13 on which it is manually tightened, that part of the collar projecting beyond the end 2a is engaged in the device until said end 2a comes into abutment against the distal portion 4a and against the inner face of the slide-way 4''a, as shown in FIG. 4. To tighten the collar, the operator presses the two handles together, which causes the two distal portions to move apart, so that the pivoting pawl is released. The pawl's gripping surface 9a abuts against the tongue of the collar by its sharp edge 9b. The continuing movement pulls the collar tongue through the collar end 2a, so that it is tightened around the elongated member 13 of roughly cylindrical section. Of course, tightening may be effected by successive operations of small amplitudes.

Figure 6:
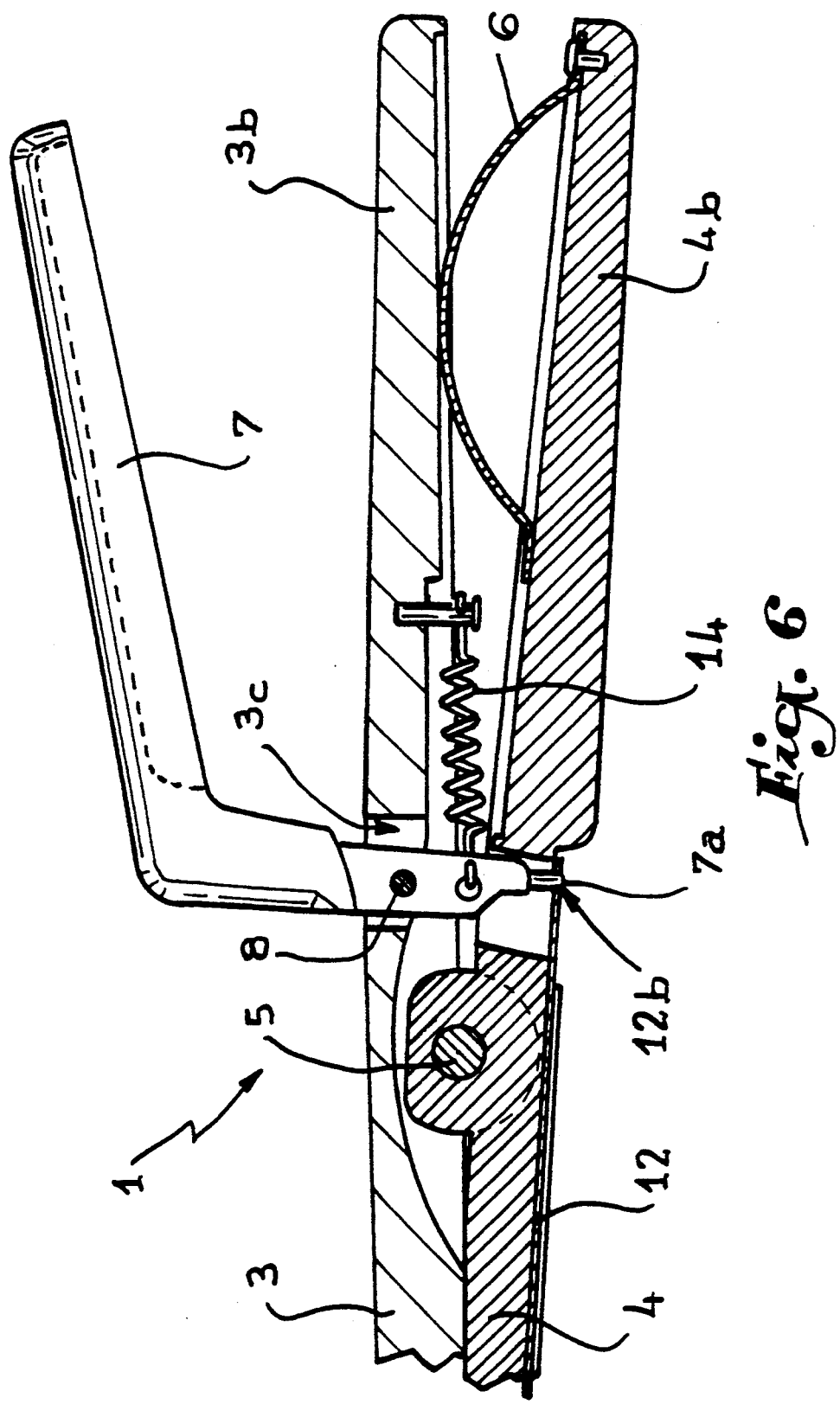
FIG. 6 is a partial longitudinal section of the device of FIG. 1, showing the articulation of its arms and the assembly of a lever for controlling the blade for cutting the collar.

As illustrated in FIG. 6, the end of the blade 12 opposite its cutting edge 12a is provided with a perforation 12b in which is engaged a pin 7a fixed to the lever 7. The lever 7 is articulated about the pin 8 and traverses an opening 3c in the handle 3d. This arm 7 is also connected to a spring 14 which maintains the lever 7 tipped so that the cutting edge of the blade 12 is, in its rest position, kept away from the opening 4'a, as indicated above and illustrated in FIG. 3.

When the collar is completely tightened around the member 13, the operator press lever 7 which slides the blade toward the collar, so that it cuts the collar in the immediate proximity of its end 2a.

The operator now merely has to release the lever 7 so that the blade is returned to its rest position. If the cerclage operation is effected in a cavity, the operator withdraws the clamp from said cavity as well as the cut collar tongue.

A device for tightening a collar with respect to an elongated member of roughly circular section has thus been produced, which allows such tightening even if said member is located in a cavity. The device according to the invention may therefore be applied to the cerclage of the cervix of the uterus of a woman or of an animal such as a ewe.

It must, of course, be understood that the foregoing description had been given only by way of example and that it in no way limits the domain of the invention which would not be exceeded by replacing the details of execution described by any other equivalents.

I claim:

1. A device for tightening a collar around a member which is oriented generally parallel to the device, the collar having an end and a tongue, the device comprising:
    a first arm having a first distal portion, a first handle, a first opening in said first distal portion, said first opening being defined by an inner surface;
    a second arm having a second distal portion, a second handle and a second opening in said second distal portion being aligned with said first opening such that the collar tongue may extend through both openings simultaneously;
    first pivot means for connecting said first and second arms about a first pivot axis, said first and second handles being disposed on opposite sides of said first pivot axis from their respective distal arm portion;
    first spring means for biasing said first and second arms so that said first and second distal portions contact in a rest position of the device, said first and second handles being movable relative to one another about said first pivot axis to separate said first and second distal portions; and
    pawl means for gripping and pulling the collar tongue through said second opening, said pawl means including a gripping surface and second pivot means connecting said pawl means to said first distal portion of said first arm, said second pivot means extending substantially perpendicularly to said first pivot axis and defining a second pivot axis, the gripping surface being disposed opposite the inner surface and further from the second arm than the second pivot axis such that a force acting on said gripping surface toward the second arm compresses said inner surface and said gripping surface toward one another to grip the collar tongue.

2. The device of claim 1, wherein the second arm further comprises an upper surface which faces the first arm, and the pawl means further comprises a bottom surface disposed substantially perpendicularly to said gripping surface and facing said upper surface such that said upper surface contacts said bottom surface when the device is in the rest position and rotates said gripping surface away from the collar tongue and from said first gripping surface.

3. The device of claim 2, further comprising pawl spring means for biasing said gripping surface against said inner surface.

4. The device of claim 1, further comprising pawl spring means for biasing said gripping surface against said inner surface.

5. The device of claim 4, further comprising:
    cutting means for severing the collar tongue, the cutting means having a sharp end disposed proximate the second opening and being movably mounted on said second arm such that the sharp end may sever the collar tongue;
    a cutting arm movably connected to the device spaced from said first and second distal portions on the opposite side of said first pivot means, the cutting arm including a cutting handle and cutter engaging means for applying a force on the cutting means to move said sharp end with respect to the tongue; and
    cutting spring means for biasing said sharp end away from the collar tongue.

6. The device of claim 5, wherein both the first and cutting spring means are spaced from said first and second distal portions on the opposite side of said first pivot means.

7. A device for tightening a collar around a member which is oriented generally parallel to the device, the collar having an end and a tongue, the device comprising:
    a first arm having a first distal portion, a first handle, and a first opening in said first distal portion, said first opening being defined by an inner surface;
    a second arm having a second distal portion, a second handle and a second opening in said second distal portion being aligned with said first opening such that the collar tongue may extend through both openings simultaneously;
    first pivot means for connecting said first and second arms about a first pivot axis, said first and second handles being disposed on opposite sides of said first pivot axis from their respective distal arm portion;
    first spring means for biasing said first and second arms so that said first and second distal portions contact in a rest position of the device, said first and second handles being movable relative to one another about said first pivot axis to separate said first and second distal portions;
    pawl means for gripping and pulling the collar tongue through said second opening, said pawl means including a gripping surface and second pivot means connecting said pawl means to said first distal portion of said first arm, said second pivot means extending substantially perpendicularly to said first pivot axis and defining a second pivot axis, the gripping surface being disposed opposite the inner surface and further from the second arm than the second pivot axis such that a force acting on said gripping surface toward the second arm compresses said inner surface and said gripping surface toward one another to grip the collar tongue;

cutting means for severing the collar tongue, the cutting means having a sharp end disposed proximate the second opening and being movably mounted on said second arm such that the sharp end may sever the collar tongue; and a cutting arm pivotably connected to the device about a third pivot axis spaced from said first and second distal portions on the opposite side of said first pivot means, the cutting arm including a cutting handle and cutter engaging means for applying a force on the cutting means to move said sharp end with respect to the tongue, said cutting handle being disposed opposite the cutter engaging means relative to the cutter pivot axis.

8. The device of claim 7, further comprising:

pawl spring means for biasing said gripping surface against said inner surface; and cutting spring means for biasing said sharp end away from the collar tongue.

9. The device of claim 8, wherein said first handle defines a slot, said cutting arm extends through said slot, and said third pivot axis is disposed on said first arm.

10. The device of claim 9, wherein said cutting means is slidably mounted to said second arm and defines a hole opposite said sharp end, and said cutter engaging means comprises a pin which fits through said hole.

11. The device of claim 10, wherein both the first and cutting spring means are spaced from said first and second distal portions on the opposite side of said first pivot means.

12. The device of claim 11 wherein the second arm further comprises an upper surface which faces the first arm, and the pawl means further comprises a bottom surface disposed substantially perpendicularly to said gripping surface and facing said upper surface such that said upper surface contacts said bottom surface when the device is in the rest position and rotates said gripping surface away from the collar tongue and from said first gripping surface.

13. The device of claim 8, wherein the second arm further comprises an upper surface which faces the first arm, and the pawl means further comprises a bottom surface disposed substantially perpendicularly to said gripping surface and facing said upper surface such that said upper surface contacts said bottom surface when the device is in the rest position and rotates said gripping surface away from the collar tongue and from said first gripping surface.

14. The device of claim 18, wherein both the first and cutting spring means are spaced from said first and second distal portions on the opposite side of said first pivot means.

* * * * *